(12) United States Patent
Malkowski (10) Patent No.: US 8,968,339 B2
(45) Date of Patent: Mar. 3, 2015

(54) SUTURING DEVICE WITH DEPLOYABLE NEEDLE

(75) Inventor: Jaroslaw T. Malkowski, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 434 days.

(21) Appl. No.: 13/300,700

(22) Filed: Nov. 21, 2011

(65) Prior Publication Data
US 2012/0150197 A1    Jun. 14, 2012

Related U.S. Application Data

(60) Provisional application No. 61/421,699, filed on Dec. 10, 2010.

(51) Int. Cl.
| A61B 17/04 | (2006.01) |
| A61B 17/062 | (2006.01) |
| A61B 17/06 | (2006.01) |
| A61B 17/00 | (2006.01) |

(52) U.S. Cl.
CPC ....... *A61B 17/0625* (2013.01); *A61B 17/06066* (2013.01); *A61B 17/00234* (2013.01); *A61B 17/0469* (2013.01); *A61B 2017/0609* (2013.01)
USPC ........................................................ 606/144

(58) Field of Classification Search
CPC .................. A61B 17/0625; A61B 17/06066; A61B 2017/0609
USPC ............................................. 606/139, 144, 1
See application file for complete search history.

(56) References Cited

U.S. PATENT DOCUMENTS

| 5,458,609 A | 10/1995 | Gordon et al. |
| 5,591,181 A * | 1/1997 | Stone et al. .................. 606/144 |
| 5,947,982 A | 9/1999 | Duran |
| 5,980,538 A | 11/1999 | Fuchs et al. |
| 6,921,408 B2 | 7/2005 | Sauer |
| 2005/0165328 A1* | 7/2005 | Heske et al. .................. 600/566 |
| 2009/0138029 A1 | 5/2009 | Saliman et al. |
| 2010/0331863 A2 | 12/2010 | Saliman et al. |
| 2011/0301619 A1* | 12/2011 | Walters ......................... 606/144 |

FOREIGN PATENT DOCUMENTS

WO    WO 00/60995    10/2000

OTHER PUBLICATIONS

European Search Report dated Apr. 5, 2013 in copending European Patent Application No. 11192873.

* cited by examiner

*Primary Examiner* — Victor Nguyen (57) ABSTRACT

A surgical apparatus for use in endoscopic and/or laparoscopic procedures is provided. The surgical apparatus has an elongated body portion, a first jaw member extending from the body portion, and a second jaw member extending from the body portion and opposing the first jaw member. The second jaw member has a split nest slide coupled thereto that is configured to position a surgical incision member in a folded or unfolded position.

15 Claims, 9 Drawing Sheets

SUTURING DEVICE WITH DEPLOYABLE NEEDLE

CROSS-REFERENCE TO RELATED APPLICATIONS

This application claims the benefit of, and priority to, U.S. Provisional Patent Application Ser. No. 61/421,699 filed on Dec. 10, 2010, the disclosure of which is hereby incorporated by reference in its entirety.

BACKGROUND

1. Technical Field

The device relates generally to surgical instrumentation and, more particularly, to a suturing apparatus adapted for use in endoscopic or laparoscopic surgical procedures.

2. Description of Related Art

Endoscopic or laparoscopic procedures are characterized by the use of an elongated cannula structure having a relatively small diameter with a proximal and distal end. The distal end of the cannula is passed through the surrounding tissue into the body cavity wherein the surgical procedure or examination is to be effected, thus providing a conduit for the insertion of surgical instrumentation. A plurality of cannula structures may be used to allow operation of a variety of instruments simultaneously during a given procedure. For example, one cannula may provide a conduit for an endoscope for vision and illumination within the operative cavity while the other cannulas may provide conduits for control of specialized surgical instruments designed for performing specific procedural functions.

Many surgical procedures call for placing stitches through tissue, a procedure traditionally accomplished by hand. Laparoscopic suturing presents a particularly challenging task, because it must be accomplished using remote instrumentation through a port that typically averages between five and ten millimeters. One instrument for facilitating laparoscopic suturing is discussed in commonly owned U.S. Pat. No. 5,591,181, the contents of which are herein incorporated by reference.

Although the suturing device described in U.S. Pat. No. 5,591,181 can be used to place laparoscopic sutures, the suturing device may require the use of a larger cannula to allow a needle to be passed through in order to place stitches through tissue. As it is generally considered desirable to reduce the size of a cannula used during a laparoscopic procedure to limit the amount of trauma to a patient as well as reduce the time it takes to heal, it would be advantageous to provide a laparoscopic suturing instrument that can pass through a smaller cannula.

SUMMARY

In an embodiment of the present disclosure, a surgical apparatus for use in endoscopic and/or laparoscopic procedures is provided. The surgical apparatus has an elongated body portion, a first jaw member extending from the body portion, and a second jaw member extending from the body portion and opposing the first jaw member. The second jaw member has a split nest slide coupled thereto that is configured to position a surgical incision member in a folded or unfolded position. The second jaw member may include a needle blade configured to secure the surgical incision member in the second jaw member and a flexible link coupled to the split nest slide. The flexible link may be configured to control the movement of the split nest slide to position the surgical incision member in a folded or unfolded position. Additionally, the first jaw member and second jaw member are rotatably connected to the body portion. The flexible link may include an elastic blade and a holding pin.

In another embodiment of the present disclosure, a method of assembling a surgical apparatus having an elongated body portion, and an end effector having a first jaw member and a second jaw member opposing the first jaw member is provided. The method includes placing the end effector assembly in an open state, attaching a split nest slide to the second jaw member and coupling the slit nest slide to a flexible link in the second jaw member using a pin. A needle blade in the second jaw member is moved in a distal direction such that an aperture in the needle blade corresponds to an aperture in the split nest slide and an aperture in the second jaw member. Then a surgical incision member is placed through the aperture of the split nest slide, the aperture of the second jaw member and the aperture of the needle blade. The needle blade is then moved in a proximal direction to secure the surgical incision member in the second jaw member.

In yet another embodiment of the present disclosure a method of using a surgical apparatus including an elongated body portion, and an end effector having a first jaw member and a second jaw member opposing the first jaw member, a split nest slide coupled to the second jaw member, a flexible link coupled to the slit nest slide and a needle blade is provided. The end effector assembly is placed in an open state to secure a surgical incision member in the second jaw member using the needle blade. The flexible link is moved in a proximal direction to place the surgical incision member in a folded position and the end effector assembly is placed in a closed state. The end effector assembly is passed through a surgical port and placed in an open state before moving the flexible link in a distal direction to place the surgical incision member in an unfolded position. When the end effector assembly needs to be removed, the flexible link is moved in a proximal direction to place the surgical incision member in a folded position. The end effector assembly is then placed in a closed state and removed through the surgical port.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION OF PREFERRED EMBODIMENTS

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Like reference numerals may refer to similar or identical elements throughout the description of the figures. As shown in the drawings and described throughout the following description, as is traditional when referring to relative positioning on a surgical instrument, the term "proximal" refers to the end of the apparatus which is closer to the clinician and the term "distal" refers to the end of the apparatus which is further away from the clinician. The term "clinician" refers to any medical professional (i.e., doctor, surgeon, nurse, or the like) performing a medical procedure involving the use of embodiments described herein.

Figure 1:
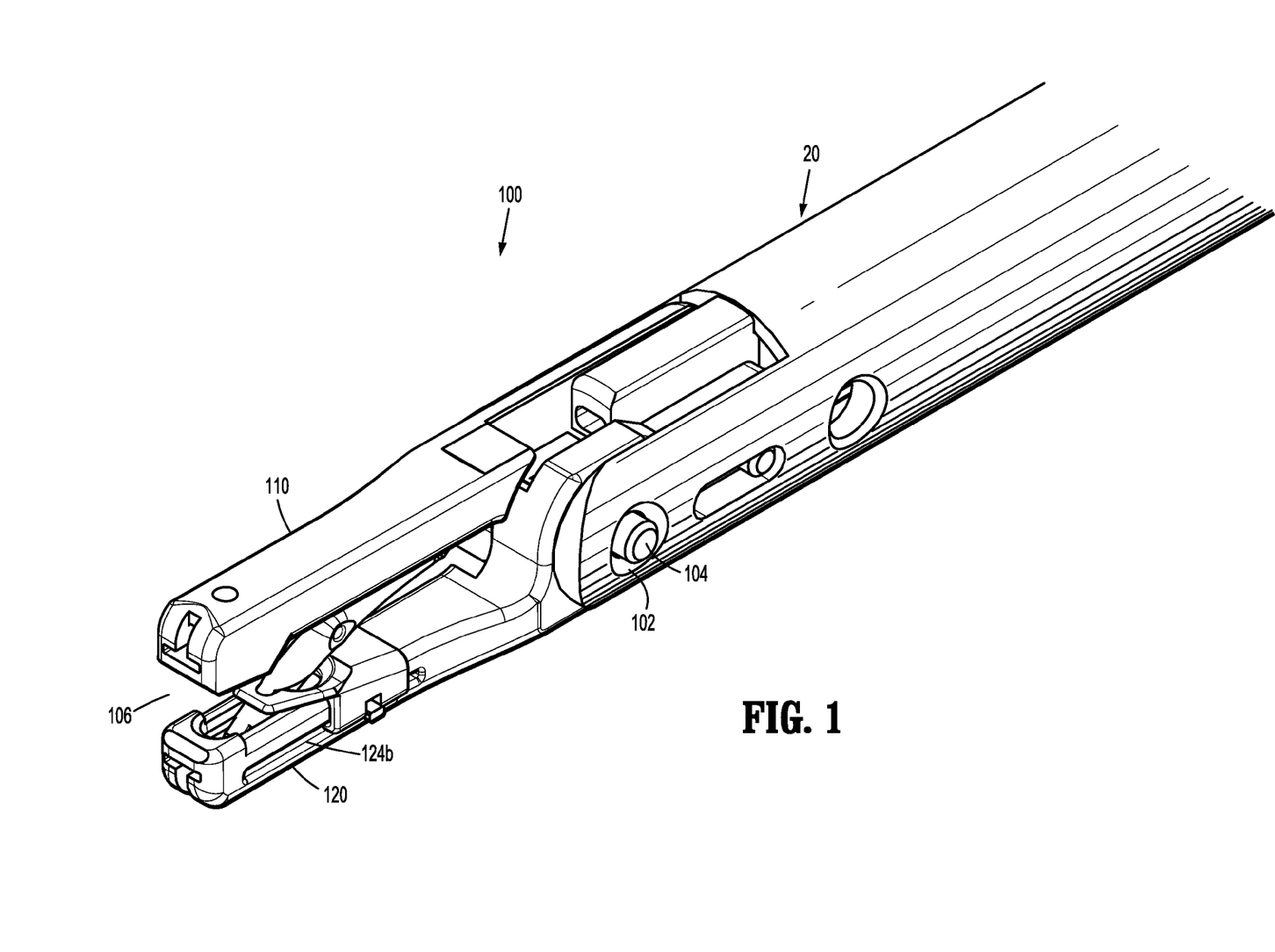
FIG. 1 is a perspective view of an end effector assembly of a surgical suturing apparatus in a closed position according to an embodiment of the present disclosure.
Figure 2:
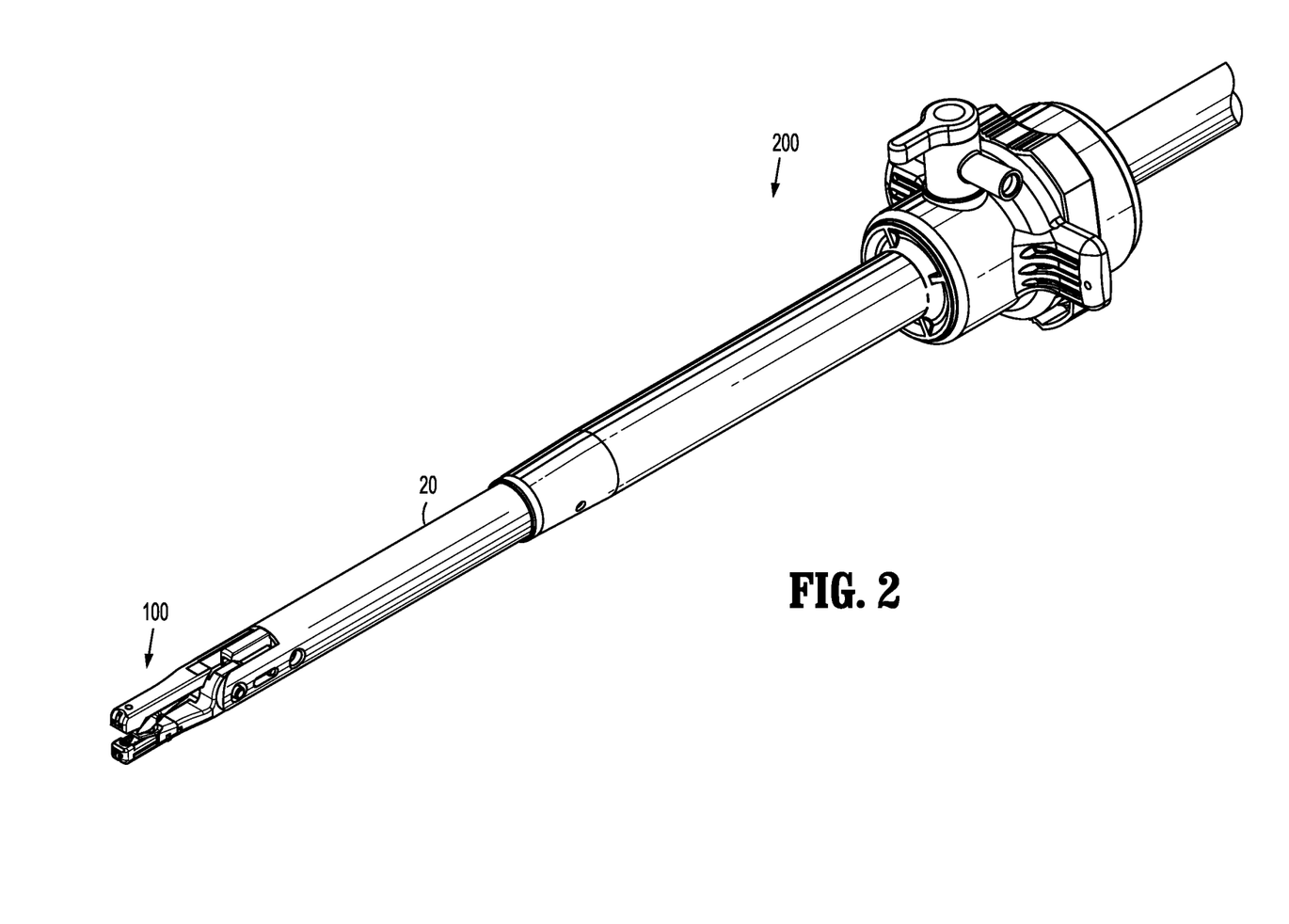
FIG. 2 is a perspective view of a surgical suturing device according to an embodiment of the present disclosure.

Referring now to the drawings and in particular to FIGS. 1 and 2, there is shown an end effector for a surgical suturing apparatus generally designated by reference numeral 100. An example of surgical suturing apparatus capable of employing end effector 100 is described in U.S. Pat. No. 5,591,181.

End effector 100 is disposed at the distal end of a shaft 20 that is coupled to a handle (not shown) of a surgical suturing apparatus and includes a pair of opposing jaw members 110 and 120. The handle is used to control the opening and closing of jaws 110 and 120 and may be designed to move in the same plane as jaws 110 and 120 to provide an ergonomic advantage. The handle may also be rotatably connected to shaft 20 to provide further ergonomic advantage. Jaw members 110 and 120 are pivotally connected to each other by pin 104 extending through aperture or hole 102. During a laparoscopic procedure, shaft 20 may be inserted through a cannula or surgical port 200

Figure 12:
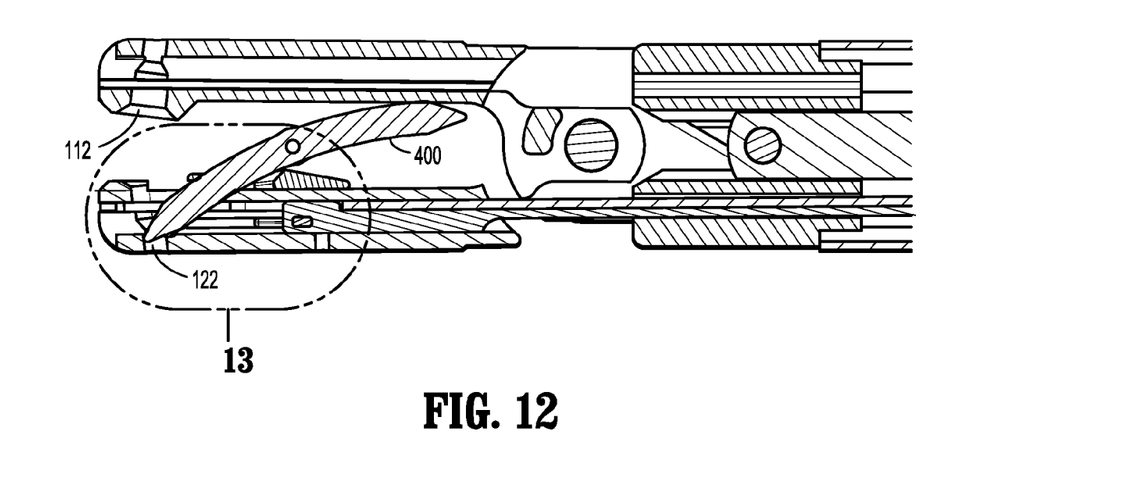
FIG. 12 is a plan view of the end effector assembly of FIG. 11.
Figure 13:
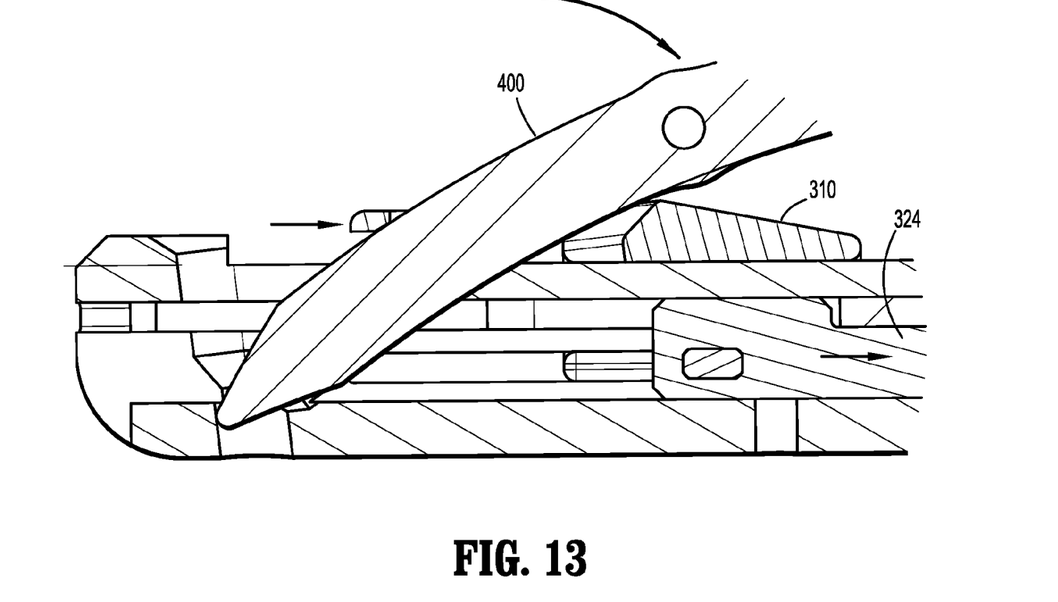
FIG. 13 a detailed view of the area outlined in FIG. 12.
Figure 14:
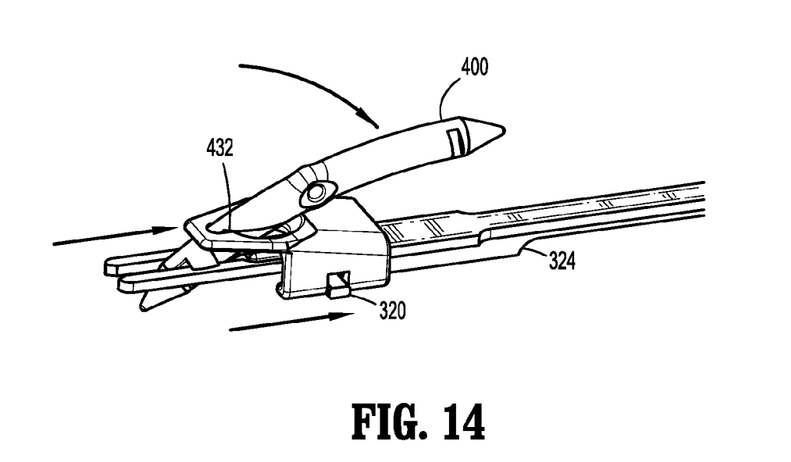
FIG. 14 is a perspective view illustrating operation of the split news needle folding mechanism.

Each jaw member 110, 120 is adapted to receive a needle 400 (FIG. 3) in recesses 112, 122 respectively (FIG. 12). Needle 400 is depicted throughout the figures as a surgical incision member (as defined above), however, the use of other varieties of surgical needles is also contemplated. When jaws 110 and 120 are closed as shown in FIG. 1, the needle 400 sits in a cavity 106 formed between jaws 110 and 120. When the jaws are opened, the needle 400 is retained in recesses 112 or 122.

Figures 3, 4:
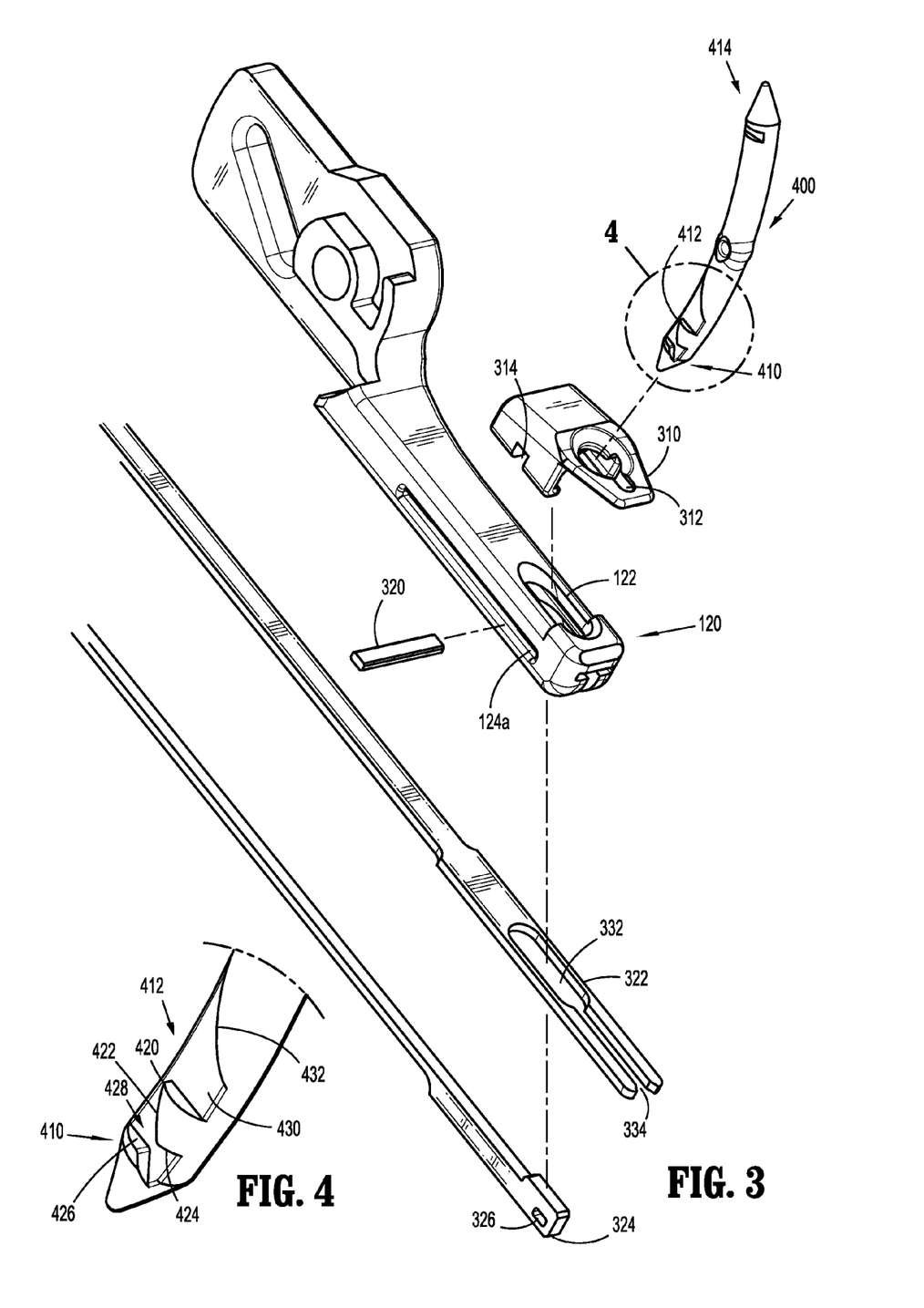
FIG. 3 is an exploded view of a jaw member of the end effector assembly depicted in FIG. 1.
FIG. 4 is a detailed view of the area outlined in FIG. 3.
Figure 8:
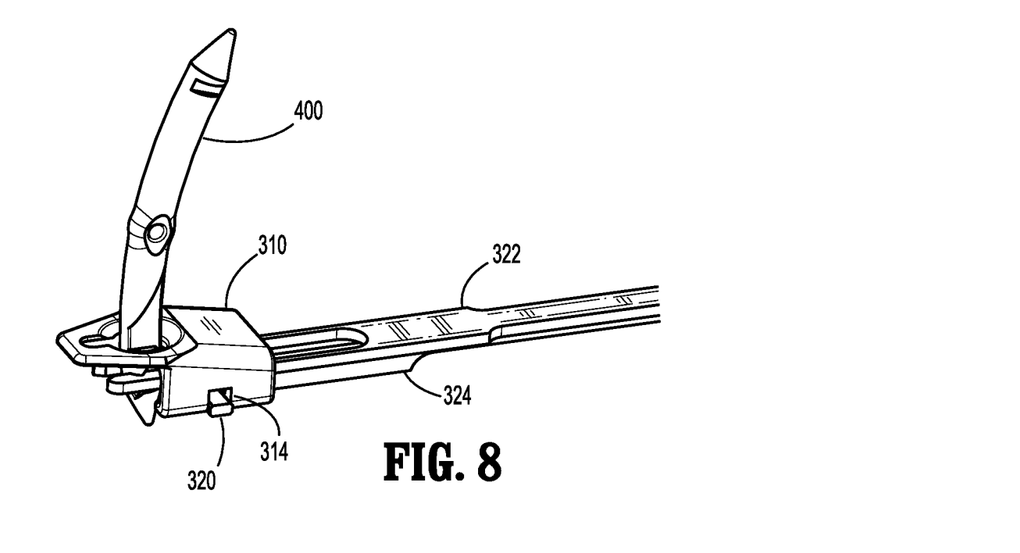
FIG. 8 is a perspective view of a jaw member of the end effector assembly of FIG. 1 with some of the parts removed.
Figure 9:
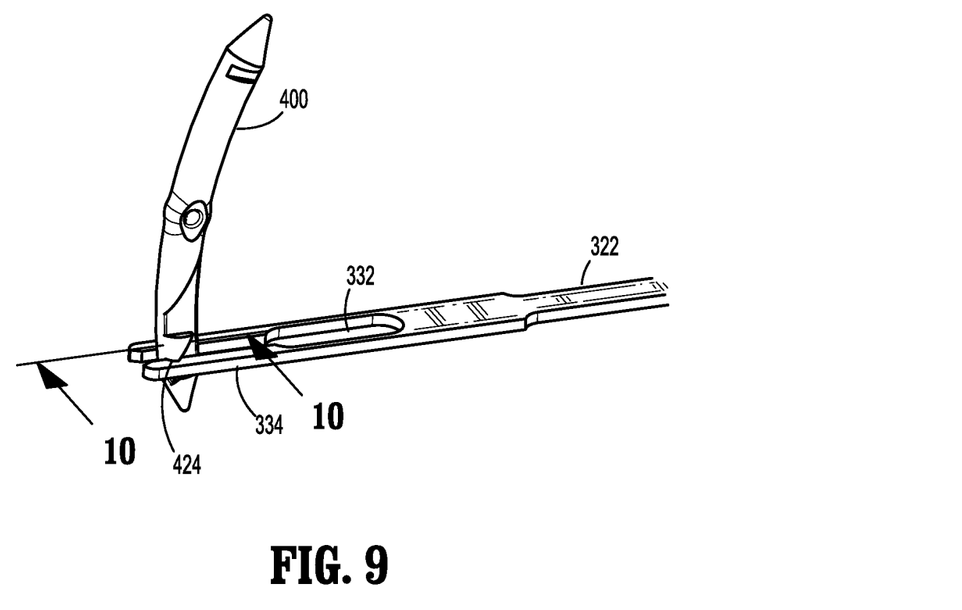
FIG. 9 is a perspective view of a needle and cam when the end effector assembly is in an open position.
Figure 10:
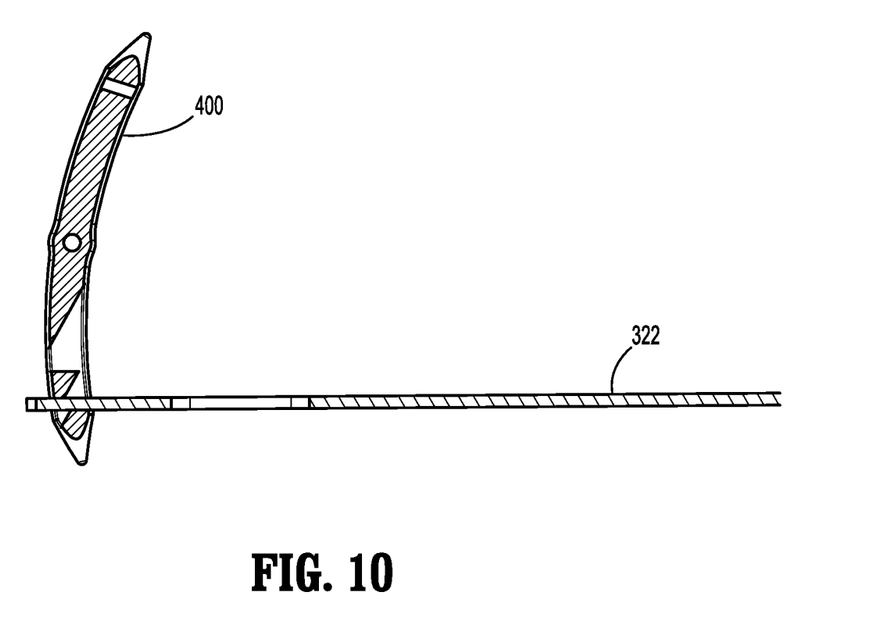
FIG. 10 is a plan view of the needle and cam in an open position taken along the line 10-10 of FIG. 9.

Referring to FIGS. 3-16, the suturing apparatus having end effector 100 will be described hereinbelow. Distal end 410 of needle 400 is placed through aperture 312 of the split nest slide 310, aperture 122 of jaw member 120 and aperture 332 of needle blade 322. Needle 400 is locked in place by a flexible needle blade 322 on the split nest side 412 of needle 400. More specifically, and as shown in FIGS. 4, 9 and 10, split nest side 412 includes a protrusion 420 having a channel 428 and 430 and edges 424 and 426. Before placing needle 400 in jaw member 120, needle blade 322 is pushed distally until aperture 332 of needle blade 322 is in line with aperture 312 of split nest slide 310 and aperture 122 of jaw member 120. After needle 400 is placed in an unfolded position in jaw member 120, needle blade 322 is pulled proximally so that channel 428 of needle 400 slides between fingers 334 of needle blade 322 while channel 430 slides between opposing edges of aperture 312 of split nest slide 310. Edges 424 and 426 abut one of fingers 334 thereby locking needle 400 in jaw member 120. Flexible needle blade 322 may be composed from a 17-4 PH SST which is a precipitation hardening martensitic stainless steel having a Rockwell hardness scale C number between 41-47. Alternatively, 301 hardened stainless steel may be used. Flexible needle blade 322 should have leaf spring properties and a good hardness to be able to hold needle 400.

Figure 7:
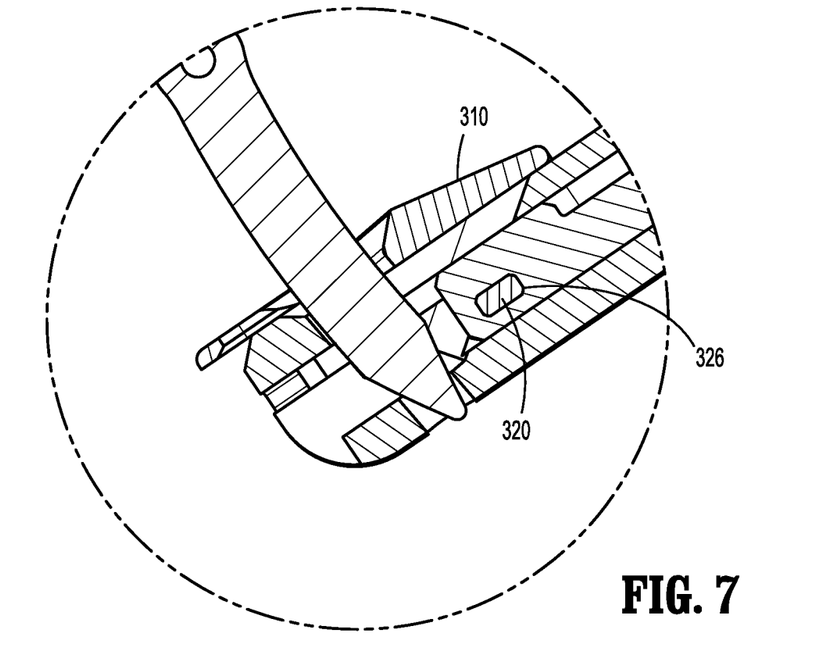
FIG. 7 is a detailed view of the area outlined in FIG. 6.

Split nest slide 310 is driven by a flexible link 324. Flexible link 324 may be composed from a 17-4 PH SST which is a precipitation hardening martensitic stainless steel having a Rockwell hardness scale C number between 41-47. Flexible link 324 may also be composed of two portions: an elastic blade; and a hard head holding pin 320. As shown in FIGS. 3, 7 and 8, split nest slide 310 has a notch 314 that corresponds to an aperture 326 in flexible link 324. A pin 320 is placed through channel 124a on one side of jaw member 120, through aperture 326 and out the other side of jaw member 120 through a corresponding channel 124b (FIG. 1). Notch 314 of split nest slide 310 rests on pin 320. As such, when flexible link 324 is moved distally or proximally, split nest slide 310 also moves distally or proximally.

Figure 5:
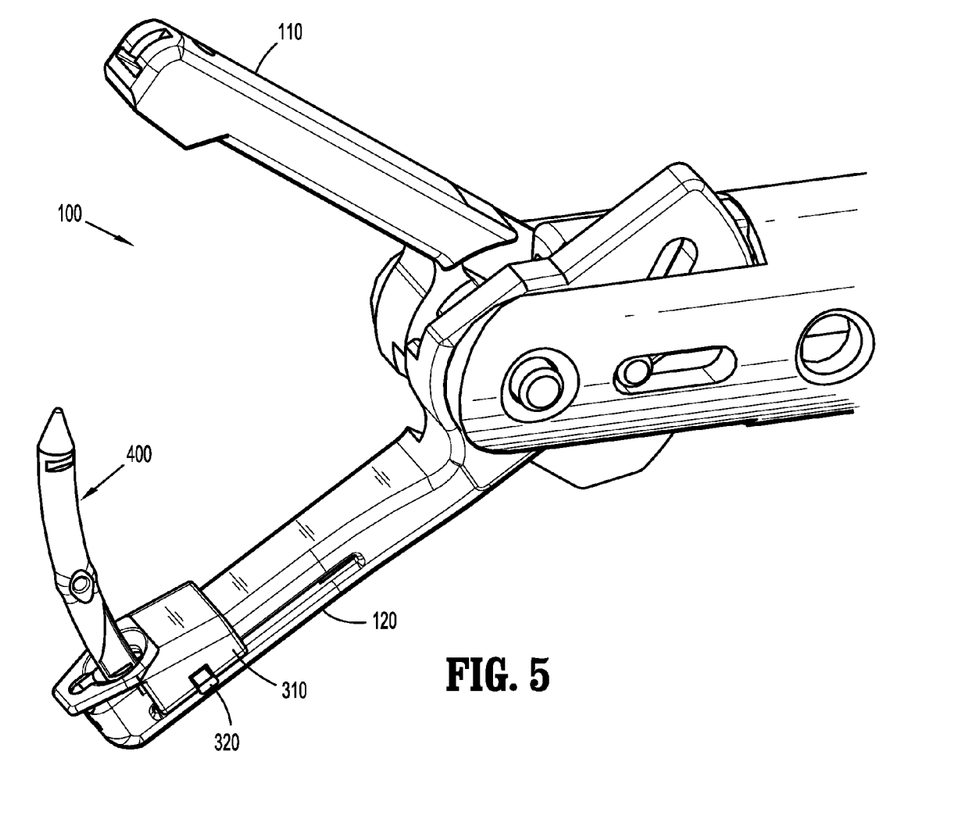
FIG. 5 is a perspective view of the end effector assembly of FIG. 1 in an open position.
Figure 6:
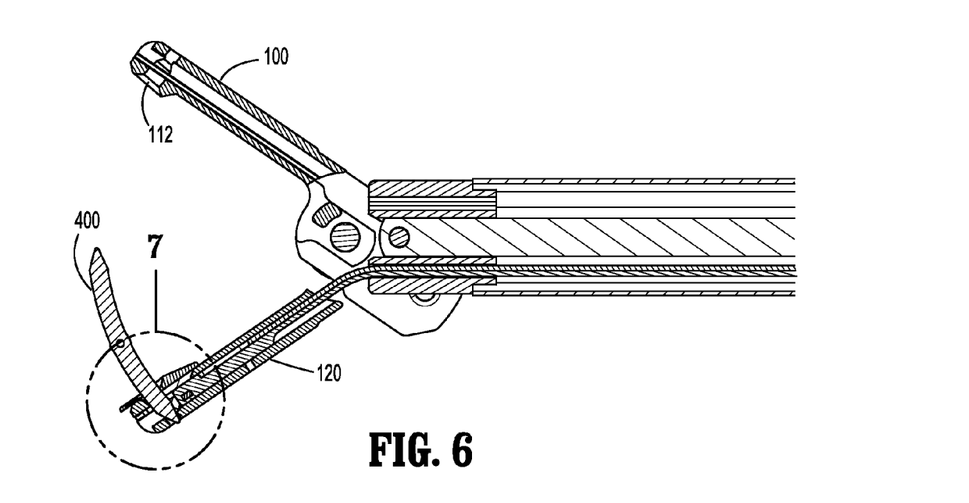
FIG. 6 is a plan view of the end effector assembly shown in FIG. 6.

FIGS. 5 and 6 depict end effector assembly in an open state with needle 400 in an unfolded position. As shown in FIGS. 5 and 6, when flexible link 324 is pushed distally, split nest slide 310 is positioned on the distal end of jaw member 120 thereby positioning needle 400 in an unfolded position.

Figure 11:
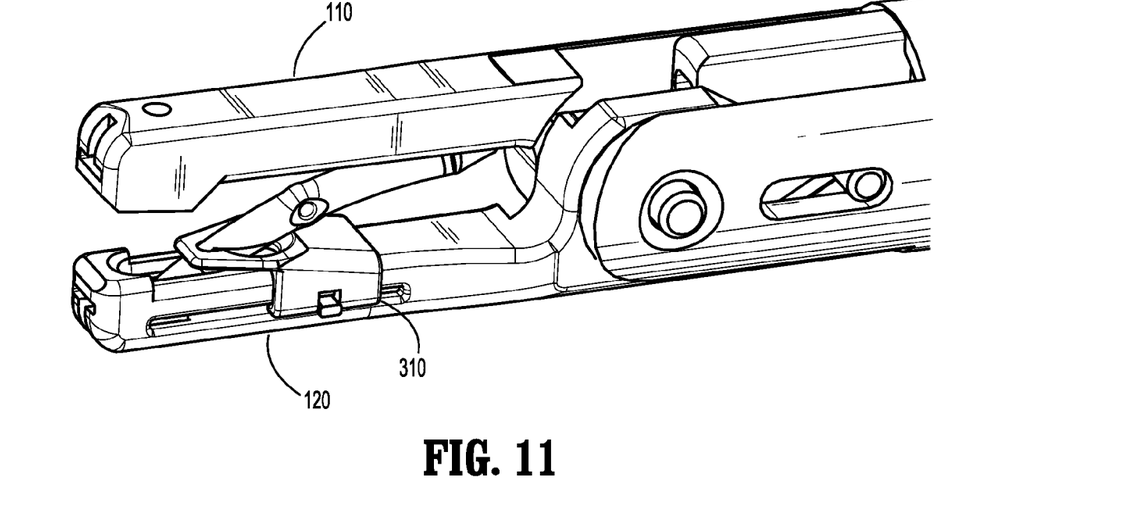
FIG. 11 is a side view of the end effector assembly of FIG. 1.
Figure 15:
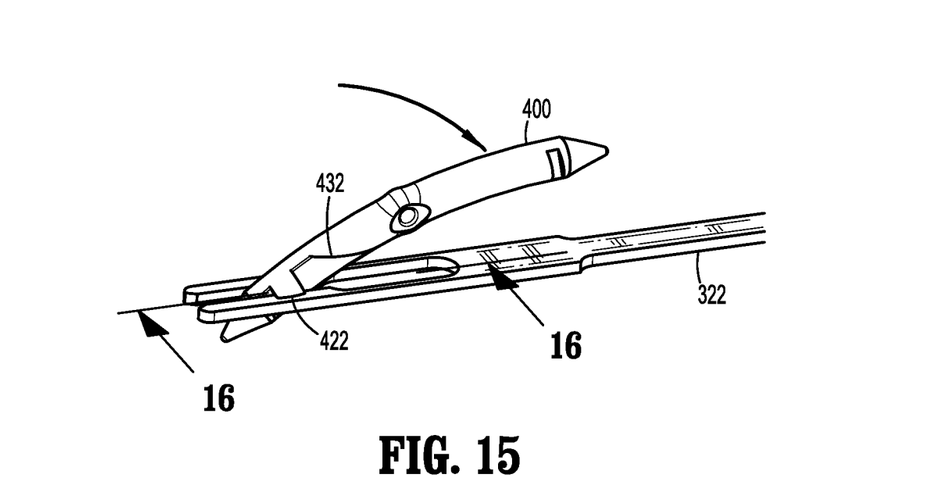
FIG. 15 is a perspective view of a needle and cam when the end effector assembly is in a closed position.
Figure 16:
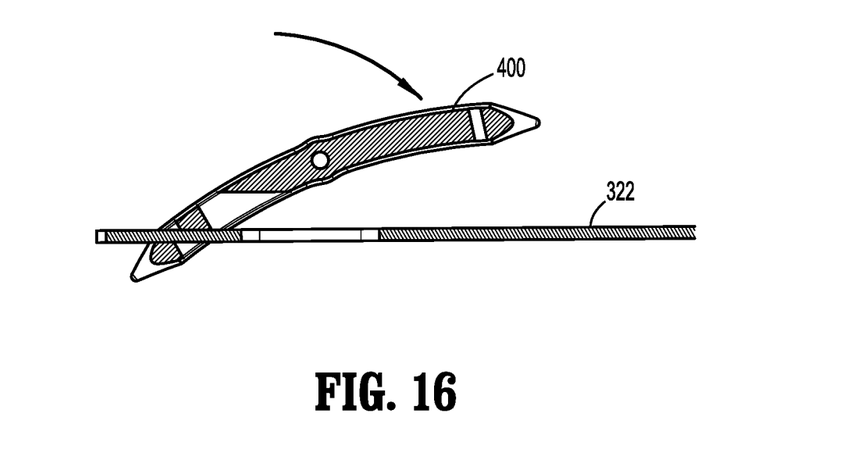
FIG. 16 is a plan view of the needle and cam in a closed position taken along the line 16-16 of FIG. 15.

FIGS. 11 through 16 depict end effector assembly 100 in a closed state with needle 400 in a folded position. As shown in FIGS. 11 and 12, when flexible link 324 is pulled proximally, split nest slide 310 is positioned near the proximal end of jaw member 120 thereby positioning needle 400 in a folded position. The folding of needle 400 is more clearly shown in FIGS. 13-16, which show flexible link 324 moving in a proximal direction. As flexible link 324 is pulled proximally, split nest slide 310 moves proximally because split nest slide 310 is coupled to flexible line 324 via pin 320. Movement of the split nest slide 310 in the proximal direction causes proximal end 414 of needle 400 to move in an arcuate direction toward jaw member 120 until edge 422 of split nest side 412 rests on one of fingers 334 of needle blade 322 (FIG. 15). Further, when split nest slide 310 is moved in the proximal direction, edge 432 engages the edges of aperture 312.

The split nest needle folding mechanism described above in accordance with an embodiment of the present disclosure permits the use of a larger needle 400 with a surgical suturing apparatus suitable for use with a smaller port or cannula thereby allowing needle 400 to be used with, e.g., a 5 mm port opening. During a surgical procedure, needle 400 is loaded into jaw member 120 as described above and folded inwards using flexible link 324 and split nest slide 310. End effector assembly 100 is placed in a closed state that secures the folded needle and is passed through port 200 (FIG. 2). After passing through port 200, end effector assembly 100 is placed in an open state and link 324 is pushed distally causing split nest slide 310 to move distally thereby placing needle 400 in an unfolded position. After completing a stitching procedure, the needle is folded inward by pulling flexible link 324 proximally and end effector 100 is placed in a closed state in order to pull end effector 100 out of port 200.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing FIGS. are presented only to demonstrate certain examples of the disclosure. Other elements, steps, methods and techniques that are insubstantially different from those described above and/or in the appended claims are also intended to be within the scope of the disclosure.

The invention claimed is:

1. A surgical apparatus comprising:
an elongated body portion;
a first jaw member extending from the elongated body portion;
a second jaw member extending from the elongated body portion opposing the first jaw member; a needle operably coupled to the second jaw member; and a split nest slide coupled to the second jaw member, the split nest slide movable relative to the second jaw member and configured to position the needle in a folded or unfolded position.

2. The surgical apparatus according to claim 1, wherein the second jaw member further comprises a needle blade configured to secure the needle in the second jaw member.

3. The surgical apparatus according to claim 1, further comprising a flexible link coupled to the split nest slide, the flexible link being configured to control the movement of the split nest slide to position a surgical incision member in a folded or unfolded position.

4. The surgical apparatus according to claim 3, wherein the flexible link comprises an elastic blade and a holding pin.

5. The surgical apparatus according to claim 1, further comprising a surgical incision member lockable in place by the split nest slide.

6. The surgical apparatus according to claim 1, wherein movement of the split nest slide relative to the second jaw member causes a surgical incision member to translate between a folded position and an unfolded position.

7. The surgical apparatus according to claim 1, wherein proximal movement of the split nest slide relative to the second jaw member causes a surgical incision member to translate from a folded position to an unfolded position.

8. A surgical apparatus comprising:
an elongated body portion;
a first jaw member extending from the elongated body portion;
a second jaw member extending from the elongated body portion opposing the first jaw member; a needle operably coupled to the second jaw member; and a split nest slide movable relative to the second jaw member and configured to translate between a first position and a second position, wherein the needle is in a folded position when the split nest slide is in the first position and in an unfolded position when the split nest slide is in the second position.

9. The surgical apparatus according to claim 8, further comprising a surgical incision member operably coupled to the second jaw member.

10. The surgical apparatus according to claim 8, further comprising a flexible link coupled to the split nest slide, the flexible link configured to control the movement of the split nest slide to position a surgical incision member in a folded or unfolded position.

11. The surgical apparatus according to claim 8, wherein proximal movement of the split nest slide relative to the second jaw member causes a surgical incision member to translate from a folded position to an unfolded position.

12. The surgical apparatus according to claim 8, wherein the second jaw member further comprises a needle blade configured to secure a surgical incision member in the second jaw member.

13. A surgical apparatus comprising:
an elongated body portion;
a first jaw member extending from the elongated body portion;
a second jaw member extending from the elongated body portion opposing the first jaw member;
a split nest slide operably coupled to the second jaw member and movable relative to the second jaw member, the split nest slide translatable between a first position and a second position; and
a flexible link operably coupled to the split nest slide, the flexible link configured to translate the split nest slide between the first position and the second position; and a needle operably coupled to the second jaw member, wherein the needle is in a folded position when the split nest slide is in the first position and wherein the needle is in an unfolded position when the split nest slide is in the second position.

14. The surgical apparatus according to claim 13, wherein proximal movement of the split nest slide relative to the second jaw member causes the needle to translate from a folded position to an unfolded position.

15. The surgical apparatus according to claim 13, wherein the second jaw member further comprises a needle blade configured to secure the needle in the second jaw member.

* * * * *